US009248101B2

(12) United States Patent
Möschwitzer et al.

(10) Patent No.: US 9,248,101 B2
(45) Date of Patent: Feb. 2, 2016

(54) METHOD FOR THE GENTLE PRODUCTION OF ULTRAFINE PARTICLE SUSPENSIONS AND ULTRAFINE PARTICLES AND THE USE THEREOF (75) Inventors: Jan Möschwitzer, Berlin (DE); Andreas Lemke, Berlin (DE)

(73) Assignee: ABBVIE DEUTSCHLAND GMBH & CO KG, Wiesbaden (DE)

( * ) Notice: Subject to any disclaimer, the term of this patent is extended or adjusted under 35 U.S.C. 154(b) by 917 days.

(21) Appl. No.: 11/911,352

(22) PCT Filed: Apr. 12, 2006

(86) PCT No.: PCT/EP2006/003377
§ 371 (c)(1),
(2), (4) Date: Oct. 12, 2007

(87) PCT Pub. No.: WO2006/108637
PCT Pub. Date: Oct. 19, 2006

(65) Prior Publication Data
US 2008/0193520 A1     Aug. 14, 2008

(30) Foreign Application Priority Data

Apr. 13, 2005  (DE) .......................... 10 2005 017 777
Nov. 5, 2005   (DE) .......................... 10 2005 053 462

(51) Int. Cl.
  C09B 69/00    (2006.01)
  A61K 8/04     (2006.01)
  A61K 9/50     (2006.01)
  C09D 5/00     (2006.01)
  A61K 9/10     (2006.01)
  A61K 9/16     (2006.01)
  B82Y 5/00     (2011.01)

(52) U.S. Cl.
  CPC  A61K 9/1694 (2013.01); B82Y 5/00 (2013.01)

(58) Field of Classification Search
  None
  See application file for complete search history.

(56) References Cited

U.S. PATENT DOCUMENTS

| 5,145,684 | A |   | 9/1992  | Liversidge |        |
|-----------|---|---|---------|------------|--------|
| 5,389,382 | A |   | 2/1995  | List       |        |
| 5,510,118 | A | * | 4/1996  | Bosch et al. | 424/489 |
| 5,858,410 | A | * | 1/1999  | Muller et al. | 424/489 |
| 5,876,756 | A |   | 3/1999  | Takada     |        |
| 5,922,355 | A | * | 7/1999  | Parikh et al. | 424/489 |
| 6,010,719 | A | * | 1/2000  | Remon et al. | 424/464 |
| 6,018,080 | A |   | 1/2000  | Dearn      |        |
| 6,190,702 | B1 |  | 2/2001  | Takada     |        |
| 6,251,945 | B1 |  | 6/2001  | Einig      |        |
| 6,607,784 | B2 |  | 8/2003  | Kipp       |        |
| 6,780,324 | B2 | * | 8/2004 | Le Garrec et al. | 210/639 |
| 6,833,192 | B1 |  | 12/2004 | Caruso     |        |
| 2001/0048947 | A1 | | 12/2001 | Rowe     |        |
| 2003/0175313 | A1 | | 9/2003  | Garrec    |        |
| 2004/0266890 | A1 | * | 12/2004 | Kipp et al. | 516/20 |

FOREIGN PATENT DOCUMENTS

| CH | 6 50 944 A5 | 5/1978 |
| DE | 199 32 157 A1 | 1/2001 |
| DE | 19932157 A1 | 1/2001 |
| DE | 10 2005 017 777 A1 | 10/2006 |
| DE | 10 2005 053 462 A1 | 5/2007 |
| EP | 1 064 088 A1 | 3/1999 |
| EP | 01 305 109 B1 | 8/2001 |
| EP | 1 443 072 A1 | 1/2003 |
| WO | WO90/13285 | * 11/1990 |
| WO | 01 03670 A1 | 1/2001 |
| WO | 2004 047977 A1 | 10/2004 |
| WO | 2006 094808 A2 | 9/2006 |
| WO | 2006/094808 A2 | 9/2006 |

OTHER PUBLICATIONS

Wise. Handbook of Pharmaceutical Controlled Release Technology (2000), p. 348.*

(Continued)

Primary Examiner — Bethany Barham
Assistant Examiner — Melissa Javier
(74) Attorney, Agent, or Firm — Jeffrey S. Melcher; Manelli Selter PLLC (57) ABSTRACT The invention describes a multistage process, for producing particles with an average particle size from 50 nm to 1000 nm in a very effective and gentle manner, wherein the solid substance (active substance) is dissolved in a solvent, this liquid containing the solid substance (active substance) in dissolved form is then frozen very rapidly, the solvent/solvents used are optionally removed from the frozen matrix obtained in a (freeze-)drying process (lyophilization) or the frozen matrix is further processed directly, the solid matrix (frozen or lyophilized) is dispersed in an external phase, a liquid medium, which can be water, a mixture of water with water-miscible liquids or a non-aqueous liquid, and the resulting dispersion is then immediately exposed to high shear and/or cavitation forces, and the forces applied result in stabilization or comminution of the resulting particles in the nanometer range. The method described is particularly suitable for the processing of thermolabile and sensitive substances, since it can be performed in a manner very gentle to the product, and the wear on the devices used can be markedly decreased by reduction of the necessary cycle number or by reduction of the power density to be applied. The nanoparticles obtained can be used in various fields, e.g. in the pharmaceutical field, in the cosmetic industry, the foodstuffs industry, the textile industry and other industrial fields.

44 Claims, 1 Drawing Sheet

(56) References Cited

OTHER PUBLICATIONS

Zahr et al. "Encapsulation of Drug Nanoparticles in Self-Assembled Macromolecular Nanoshells", Langmuir, 21, 2005, pp. 403-410.*
Yeo et al. "Microencapsulation Methods for Delivery of Protein Drugs", Biotechnol. Bioprocess Eng, 6, 2001, pp. 213-230.*
B. Rabinow, nanosuspensions in drug delivery, Nat. Rev. Drug Discov. Sep. 2004, 3(9), 785-796.
Merisko-Liversidge E. Nanocrystals: Resolving Pharmaceutical Formulation Issues associated with poorly water-soluble Compounds. In: Marty JJ, editor. Particles; 2002; Orlando: Marcel Dekker; 2002.
Merisko-Liversidge E, Liversidge GG, Cooper ER. Nanosizing: a formulation approach for poorly water-soluble compounds. European Journal of Pharmaceutical Sciences 2003; 18(2):113-120.
V.B. Patravale, Nanosuspensions: a promising drug delivery strategy, Journal of Pharmacy and Pharmacology, 56(7) 827-840.
Buchmann S, Fischli, W., Thiel, F. P., Alex, R. Aqueous microsuspension, an alternative intravenous formulation for animal studies. In: 42nd Annual Congress of the International Association for Pharmaceutical Technology (APV); 1996; Mainz; 1996. p. 124.
Muller RH, Jacobs C, Kayser O. Nanosuspensions as particulate drug formulations in therapy: Rationale for development and what we can expect for the future. Advanced Drug Delivery Reviews 2001;47(1):3-19.
Rudolf Voigt, Pharmaceutical Technology for Study and Profession, Ullstein Mosby, p. 59-60.
Rios Maribel: "Bringing Formulations to Size: . . . " Pharmaceutical Technology 2004 28(11) pp. 40-53.
Rainer H. Müller, Jan Möschwitzer and Faris Nadiem Bushrab, Manufacturing of nanoparticles by milling and homogenisation techniques, eds. Gupta, Kompella, Publisher: Marcel Dekker, submitted for printing.
Sucker, H., Hydrosols an alternative for the parenteral use of poorly water-soluble active substances, in: Müller, R. H., Hildebrand, G. E., (Eds.), Pharmaceutical Technology: Modern Drug Forms, 2nd Edition, 1998, WVG, Stuttgart.
Office Action issued in German counterpart application dated Jun. 12, 2006.
Wolf, et. al., "Stabilisation and determination of the biological activity of L-Asparaginase in poly (d,l-lactide-co-glycolide) nanospheres," International Journal of Pharmaceutics, 256 (2003) pp. 141-152, XP-002421906.
Tracy, "Development and Scale-up of a Microsphere Protein Delivery System" Piotechnol. Prog. 14 (1998) pp. 108-115.
Tracy, "Development and scale-up of a microsphere protein delivery system," Biotechnology Progress, vol. 14, No. 1, Jan. 1998, pp. 108-115.
Wolf, et. al., "Stabilization and determination of the biological activity of L-asparaginase in poly(D,L-lactide-co-glycolide) nanospheres," International Journal of Pharmaceutics 30, Apr. 30, 2003, vol. 256, No. 102, pp. 141-152.
International Search Report.

\* cited by examiner

METHOD FOR THE GENTLE PRODUCTION OF ULTRAFINE PARTICLE SUSPENSIONS AND ULTRAFINE PARTICLES AND THE USE THEREOF

This application is a national stage entry under 35 U.S.C. 371 of PCT/EP2006/003377, filed 12 Apr. 2006, and claims foreign priority under 35 U.S.C. 119 and 365 to German Patent Application Serial Nos. 102005053462.7, filed 5 Nov. 2005, and 102005017777.8, filed 13 Apr. 2005.

1. FIELD OF THE INVENTION

The invention describes a method for the gentle production of ultrafine particle suspensions and ultrafine particles, which/whose particles have an average size in the nanometer range, for the pharmacy, cosmetics, food production and agriculture fields.

2. THE STATE OF THE ART

On account of the techniques used nowadays for the discovery of new drug candidates (e.g. high-throughput screening, molecular modelling, receptor fit techniques) (B. Rabinow, nanosuspensions in drug delivery, Nat. Rev. Drug Discov. September 2004, 3(9), 785796), ever more active substances which come out of pharmaceutical development, although of particularly good activity, are at the same time only very slightly soluble or practically insoluble (Merisko-Liversidge E. Nanocrystals: Resolving Pharmaceutical Formulation Issues associated with poorly water-soluble Compounds. In: Marty J J, editor. Particles; 2002; Orlando: Marcel Dekker; 2002). As a result, their bioavailability is markedly limited, particularly after oral or topical application. Parenteral administration is likewise rendered difficult by the poor solubility and the large necessary injection volumes associated with this. The use of injectable solvent mixtures (e.g. water-ethanol mixtures) or organic solvents (e.g. polyethylene glycol), even with recourse to solubilising agents often results in painful injections and hence must also be seen as a disadvantage.

One possible approach to improving the bioavailability on the basis of increased dissolution rate and increased saturation solubility is offered by nanosizing, in other words decreasing the particle size to a range less than 1000 nm. (Merisko-Liversidge E, Liversidge G G, Cooper E R. Nanosizing: a formulation approach for poorly water-soluble compounds. European Journal of Pharmaceutical Sciences 2003; 18(2):113120.) The small particle size on the one hand results in a greatly increased total surface area and on the other in a more marked curvature of the particle surface. This results in an increased solution pressure in accordance with the Kelvin equation and an increase in the saturation solubility associated therewith. In accordance with the Noyes-Whitney equation, the increase in the saturation solubility and the markedly increased surface area result in an increased dissolution rate. Accordingly, through nanosizing of drugs, as compared to micronised drug, larger quantities of dissolved active substance are available in a shorter time, as a result of which in the case of BSC (biopharmaceutical specification class) Class II drug substances, the bioavailability can be markedly improved.

Class II (BSC II) drug substances are those which rapidly permeate after oral administration, but whose bioavailability is markedly limited owing to a slow dissolution rate/low saturation solubility.

A great variety of methods have been described for producing active substances with a particle size in the nanometer range. In principle, a distinction is made between "bottom-up" and "top-down" technologies. In the "top-down" technologies, the starting point is larger drug substance crystals, which are mostly micronised in an initial production step by means of milling processes (such as for example air-jet milling). In the use of "top-down" technologies, it is generally assumed that prior micronisation of the starting material leads to better nanosizing. (V. B. Patravale, Nanosuspensions: a promising drug delivery strategy, Journal of Pharmacy and Pharmacology, 56(7) 827-840).

For the actual nanosizing, various techniques are described.

U.S. Pat. No. 5,145,684 describes the wet milling of drug substances with ball mills in order to reduce the size of drug substance crystals dispersed in surfactant solutions. The particle size of the "macrosuspension" is reduced by the mill balls and their motion. A disadvantage of this technology is the need for the use of micronised starting materials, possible contamination of the product due to attrition from the mill balls (Buchmann S, Fischli, W., Thiel, F. P., Alex, R. Aqueous microsuspension, an alternative intravenous formulation for animal studies. In: $42^{nd}$ Annual Congress of the International Association for Pharmaceutical Technology (APV); 1996; Mainz; 1996. p. 124) and the marked dependence of the milling result and the necessary milling time on the substance properties of the starting material. Depending on the substance to be milled, the achievable particle sizes are typically below 400 nm; often a particle size of 200-300 nm can be achieved. In order to obtain particle sizes in the range from 100 nm or below, however, very long milling times and special techniques (e.g. changing of the ball size) are necessary, which impedes and markedly prolongs the process operation.

An alternative production method is the use of high-pressure homogenisers, i.e. methods which are based on the piston-gap principle or the jet-stream principle (Microfluidizer Technology, Microfluidics Inc. (U.S. Pat. No. 6,018,080)). The principle of the microfluidizer is the frontal impact of two jets at very high velocity, wherein the collision of the particles results in their pulverisation. Disadvantages of this method are the number of cycles necessary (often more than 50 cycles) and potential contamination with residual microparticles.

In the use of piston-gap homogenisers, the macrosuspension is pressed through a very narrow gap, which depending on the pressure used and the viscosity of the dispersion medium has a size of 5-20 μm (Rainer H. Müller, Jan Möschwitzer and Faris Nadiem Bushrab, Manufacturing of nanoparticles by milling and homogenisation techniques, eds. Gupta, Kompella, Publisher: Marcel Dekker, submitted for printing). Here the high flow rate leads to cavitation forces, and in addition particle collisions and shear forces arising likewise result in particle pulverisation. The patent U.S. Pat. No. 5,858,410 describes the use of piston-gap homogenisers for the pulverisation of particles dispersed in pure water-surfactant mixtures. On the other hand, WO-A 0103670 describes the use of this technique to homogenise particles, which are dispersed in non-aqueous media or in mixtures of water with water-miscible liquids. The particle sizes attainable with piston-gap homogenisers here lie in the range from ca. 200-600 nm depending on the size and properties of the starting materials used and the dispersion media used and the power density applied, and in the range from about 700-900 nm in the case of very hard materials (Muller R H, Jacobs C, Kayser O. Nanosuspensions as particulate drug formulations in therapy: Rationale for development and what we can expect for the future. Advanced Drug Delivery Reviews 2001; 47(1):319).

With the "top-down" techniques described above, it is to this day almost or completely impossible at acceptable cost to obtain nanosuspensions with an average particle size of much below 100 nm and to produce a maximal particle size in the range from 100-200 nm.

In the use of the so-called "bottom-up" technologies, the starting point is drug substance solutions, i.e. molecularly ultrafinely divided drug substance molecules. If this solution is added at an appropriate rate to a non-solvent which is however miscible with the solvent used in the first step, very small active substance crystals precipitate, which however grow with time into stable, larger crystals. This method is already very old and is described as "via humida paratum" (prepared by the liquid route).

In order to retard the growth of the particles, surfactants or polymeric stabilisers are generally used. This technique is referred to as the hydrosol technique and is described in U.S. Pat. No. 5,389,382. Later, some modifications of this precipitation principle were described (see U.S. Pat. No. 6,251,945). The main problem is to stabilise the precipitated crystals in the nanometer range. The nanocrystals try to grow and form microcrystals. In order to prevent this, immediate drying of the suspension produced, e.g. by lyophilisation (Sucker, H., Hydrosols an alternative for the parenteral use of poorly water-soluble active substances, in: Müller, R. H., Hildebrand, G. E., (Eds.), Pharmaceutical Technology: Modern Drug Forms, $2^{nd}$ Edition, 1998, WVG, Stuttgart) can be used. An alternative approach is the precipitation of the particles followed by the input of energy (e.g. via shear forces or ultrasound (U.S. Pat. No. 6,607,784). These forces can be applied for example using high-speed mixers or various high-pressure homogenisers (e.g. devices from the firms APV Gaulin, NiroSoavi or Avestin) or in case of the use of ultrasound using devices from the firm Sonics. Through the treatment of the precipitated particles with such forces, a stabilisation of the particle size is achieved and the crystals do not alter their size during storage, or only insignificantly, in contrast to the crystals which have not been treated with shear forces. A disadvantage of this technique (U.S. Pat. No. 6,607, 784) is that, at least in most cases, it is necessary to remove the solvent. Furthermore, only active substances for which there is at least one good solvent and at least one non-solvent which is miscible with the solvent can be processed. A further disadvantage is that in general every solvent is at least to a certain extent soluble in the non-solvent (e.g. water); this means that during subsequent removal of the solvent used a certain residual content thereof always remains in the water. In contrast to the teaching of U.S. Pat. No. 6,607,784, in which the precipitation of the poorly soluble active substance is effected before the application of force, a technique is described in the patent application US-A 2004/0266890 wherein the process of mixing the liquids and the application of the force take place in a device specially designed for this. It is necessary for this that the liquid streams used are in a particular configuration to one another. The particle sizes achievable with the use of this new technology, especially in the concurrent modification ($4^{th}$ process category) were not defined. However, particle sizes in the range from 10 nm to 10 µm were cited, without giving specific examples of the claimed 10 nm.

From the examples presented, it becomes clear that with the hitherto known methods a rational production of storage- and long-term stable, ultrafine nanosuspensions with an average particle size in the range from 50 nm to below 1000 nm, preferably 50 nm to 600 nm, particularly preferably from 50 nm to 200 nm, can at present only be achieved with relative difficulty and with high force or energy consumption.

In contrast to this, the present invention concerns a method by means of which the problems described above can be solved.

The present invention describes a multistage process wherein a solid substance poorly soluble or insoluble in water is dissolved in a suitable solvent, the resulting solution is then frozen, the resulting frozen solid matrix is then in a first embodiment mode completely or partially freed from the solvent used for example by freeze-drying (lyophilisation) or in a second embodiment mode the frozen solid matrix is further processed without drying. The resulting solid matrix, frozen or lyophilised, is dispersed in a dispersion medium (external phase). Forces (e.g. ultrasound, cavitation and/or shear forces) are applied to this dispersion so that a suspension with an average particle size in the range from 50 nm to below 1000 nm is formed, which either itself serves as the product or is further processed.

The method according to the invention for the careful production of ultrafine particle suspensions according to claim 1 is characterised in that
a) a solid substance insoluble in water or poorly soluble in water is dissolved in a suitable solvent,
b) the solution from a) is then frozen with the formation of a solid matrix,
c) optionally, the solvent is removed from the solid matrix in the frozen state formed in b) by drying, in particular lyophilisation,
d) the solid matrix formed in b), which has optionally been dried, in particular lyophilised, in accordance with c), is dispersed in the frozen state in a dispersion medium, and
e) medium to high forces are then applied to the dispersion produced in d) prior to the melting of the frozen, dispersed, solid matrix, so that a particle suspension is formed, whose average particle size, determined by photon correlation spectroscopy (PCS), lies below 1000 nm, in particular in the range from 50 to <1000 nm, preferably below 800 nm, preferably in the range from 50 to 600 nm, and in particular below 400, preferably in the range from 50 to 200 nm, and especially below 100 nm.

Preferred embodiments are subject matter of the subclaims.

In particular, according to a further preferred embodiment, the invention includes a method for the especially effective, surfactant-free production of surface-modified active substance nanoparticles by means of high-pressure homogenisation.

The production of active substance nanoparticles is of increasing economic importance, in particular when the active substance nanoparticles (general term for active substance particles with an average particle size of <1000 nm) are drug substance nanocrystals.

Crystalline, solid particles with an average particle size of 1 to 1000 nm are described as nanocrystals (generally active substance nanocrystals, especially drug substance nanocrystals). Depending on the production method, they can also be nanoparticles with amorphous regions in some cases. Below, the terms active substance nanoparticle and drug substance nanocrystal are used synonymously.

Dispersions which contain active substance nanoparticles dispersed in a liquid phase are also described below as nanosuspensions.

According to this preferred embodiment, the surface of these active substance nanocrystals/drug substance nanocrystals can (with surface modification) also be coated with oppositely charged polyelectrolyte layers, and the active substance nanoparticles or drug substance nanocrystals then serve as template particles.

The invention also includes the use of the suspensions produced or of the particles contained therein for pharmaceutical and cosmetic application, preferably in the form of tablets and capsules, creams, ointments or powders for reconstitution before use or for the production of pharmaceutical and cosmetic preparations, preferably in the form of tablets and capsules, creams, ointments or powders for reconstitution before use.

The solid substance to be processed or to be dissolved is in particular a drug active substance, a cosmetic active substance, an additive for foodstuffs, a dye or a pigment.

The medium to high forces used in step e) are in particular shear, cavitation, milling and/or ultrasound forces, which are in particular applied via high-pressure homogenisers, jet-stream devices, rotor-stator colloid mills, ball mills, high-shear mixers or ultrasound apparatus, and the device used in each case preferably operates with a power density of $10^6$ to $10^{13}$ W/m$^3$, in particular in the range from $10^9$ to $10^{13}$ W/m$^3$.

Solvents used for the dissolution of the solid substance insoluble or poorly soluble in water include hydrophilic liquids, in particular alcohols, preferably methanol, ethanol and isopropanol, mixtures of water with liquids completely or partially miscible with water or hydrophilic liquids, in particular alcohols, preferably methanol, ethanol or isopropanol or other organic solvents, or liquids immiscible with water, in particular chloroform or dichloromethane, and preferred solvents are N-methyl-2-pyrrolidinone, 2-pyrrolidone, dimethylacetamide, ethanol, methanol, isopropanol, acetone, chloroform, dichloromethane, dimethyl sulphoxide, n-propanol, glycerine, ethylene glycol, dimethylformamide, dimethylacetamide or acids and bases, in particular hydrochloric acid, sulphuric acid, acetic acid, formic acid, fumaric acid, triethanolamine, pyridine and ammonia, and if necessary a mixture of two or more of the same is used.

The solid substance solution produced in a) can contain one or more further additives and/or dispersion-stabilising substances, in particular surfactants, stabilisers of the antiflocculant and polymer type, and inert fillers, wherein the concentrations per component, based on the weight, preferably lie in the range from 1-90%, in particular from 1-20% and preferably below 10%, ideally below 0.01-5%.

Typical surfactants or stabilising substances which can be added to the solvent are for example compounds from among the poloxamers, poloxamines, ethoxylated mono- and diglycerides, ethoxylated lipids and lipoids, ethoxylated fatty alcohols and alkylphenols, ethoxylated fatty acid esters, polyglycerine ethers and ester, lecithins, esters and ethers of sugars or sugar alcohols with fatty acids or fatty alcohols, phospholipids and sphingolipids, sterols, esters or ethers thereof and mixtures thereof of these compounds. In addition, egg lecithin, soya lecithin or hydrogenated lecithins, mixtures thereof or mixtures of one or both lecithins with one or more phospholipid components, cholesterol, cholesterol palmitate, stigmasterol or other sterols are also possibilities for addition to the solution.

Under some circumstances, it can be necessary to add further substances to the solution in order to influence the properties of the solution itself or the properties of the solid matrix produced from the solution. Possibilities for this include inter alia: diacetyl phosphate, phosphatidyl-glycerol, saturated or unsaturated fatty acids, sodium cholate, antiflocculants or amino acids, and cellulose ethers and esters, polyvinyl derivatives, alginates, xanthans, pectins, polyacrylates, poloxamers and poloxamines, polyvinyl alcohol, polyvinylpyrrolidone or glucose, mannose, trehalose, mannitol and sorbitol, fructose, sodium citrate, sodium hydrogen phosphate, sodium dihydrogen phosphate, sodium chloride, potassium chloride and glycerine. If necessary, dyes, either in dissolved form or in insoluble form as pigments, can also be added to the solvent.

Heat is then removed from this solution which contains one or more dissolved substances and can in addition contain one or more additives in a rapid step, so that a completely frozen matrix is formed. This can for example be effected by introducing this solution into liquid nitrogen, which on account of the low temperature of ca. minus 195° C. results in immediate freezing of the solution.

The solid substances to be processed can derive from a great variety of fields, i.e. pharmaceutical active substances, cosmetic active substances, but also additives for the foodstuffs industry, and materials for other industrial fields, which should preferably be in the form of finely crystalline material (e.g. micronised, e.g. particle size in the range from 1-10 μm), such as for example dyes and colorant pigments for paints and lacquers or for cosmetic applications, can be processed.

Pharmaceutical active substances can derive from the therapeutic fields cited below (optionally in the form of their low water-soluble form, e.g. as the base instead of the hydrochloride):

Examples of drug substance groups for processing into a nanosuspension are:

1. Analgesics/Antirheumatic agents
   e.g. morphine, codeine, piritramid, fentanyl, levo-methadone, tramadol, diclofenac, ibuprofen, dexibuprofen, ketoprofen, dexketoprofen, meloxicam, indomethacin, naproxen, piroxicam, rofecoxib and celecoxib,
2. Antiallergic agents
   e.g. pheniramine, dimetindene, terfenadine, astemizole, loratidine, desloratadine, doxylamine, meclozine, fexofenadine and mizolastin,
3. Antibiotics/Chemotherapeutic agents
   e.g. rifamoicin, ethambutol, thiazetazon, buparvaquon, atovaqon and tarazepid,
4. Antiepileptic agents
   e.g. carbamazepine, clonazepam, mesuximid, phenytoin and valproic acid,
5. Antimycotic agents
   a) internal:
      e.g. natamycin, amphotericin B, miconazole and itraconazole
   b) external apart from these:
      e.g. clotrimazole, econazole, fenticonazole, bifonazole, ketoconazole and tolnaftat,
6. Corticoids (for internal use)
   e.g. aldosterone, fludrocortisone, betamethasone, dexamethasone, triamcinolone, triamcinolone acetonide, fluocortolone, hydrocortisone, hydrocortisone acetate, prednisolone, prednylidene, cloprednol, budesonid and methylprednisolone,
7. Dermatological agents
   a) Antibiotics:
      e.g. tetracycline, erythromycin, framycetin, tyrothricin and fusidic acid
   b) Virostatic agents as above, apart from these:
      e.g. vidarabin,
   c) Corticoids as above, and also:
      e.g. amcinonide, fluprednidene, alclomethasone, clobetasol, halcinonid, fluocinolone, clocortolone, flumethasone, diflucortolone, fludroxycortide, halomethasone, desoximethasone, fluocinolide, fluocortin butyl, fluprednidene, prednicarbate and desonide, 8. Hypnotics and sedatives
    e.g. cyclobarbital, pentobarbital, methaqualone and benzodiazepines (flurazepam, midazolam, nitrazepam, lormetazepam, flunitrazepam, triazolam, brotizolam, temazepam and loprazolam),
9. Immunotherapeutic agents and cytokines
    e.g. azathioprin and cyclosporin,
10. Local anaesthetics
    a) internal:
        e.g. butanilicaine, mepivacaine, bupivacaine, etidocaine, lidocaine and articaine
    b) external apart from these:
        e.g. oxybuprocaine, tetracaine and benzocaine,
11. Migraine drugs
    e.g. lisuride, methysergide, dihydroergotamine, ergotamine, triptanes (such as for example zolmitriptan, sumatriptan and rizatriptan),
12. Narcotic agents
    e.g. methohexital, propofol, etomidate, ketamine, thiopental, droperidol and fentanyl,
13. Parathyroid hormones, calcium metabolism regulators
    e.g. dihydrotachysterol,
14. Ophthalmic drugs
    e.g. cyclodrin, cyclopentolate, homatropin, tropicamide, pholedrin, edoxudin, aciclovir, acetazolamide, diclofenamide, carteolol, timolol, metipranolol, betaxolol, pindolol, bupranolol, levobununol and carbachol,
15. Psychotropic drugs
    e.g. benzodiazepines (lorazepam and diazepam) and clomethiazole,
16. Sex hormones and inhibitors thereof
    e.g. anabolic agents, androgens, anti-androgens, gestagens, oestrogens and anti-oestrogens,
17. Cytostatic agents and metastasis inhibitors
    a) Alkylating agents such as melphalan, carmustin, lomustin, cyclophosphamide, ifosfamide, trofosfamide, chlorambucil, busulfan, prednimustin and thiotepa
    b) Antimetabolites such as fluorouracil, methotrexate, mercaptopurine and thioguanine
    c) Alkaloids such as vinblastine, vincristine and vindesine,
    d) Antibiotics such as dactinomycin,
    e) Taxol and related or analogous compounds,
    f) Dacarbazine, estramustin and ethoposide
    g) Oxalipantin,
    h) Platinum compounds e.g. cisplatin and carboplatin,
18. Sartans
    Olmesartan, candesartan, valsartan and losartan
19. Fibrates
    Bezafibrate, fenofibrate, ethofibrate and ethophylline clofibrate,
20. Statins
    Pravastatin, simvastatin, cerivastatin, atorvastatin, fluvastatin, lovastatin and rosuvastatin,
21. HIV drugs
    Abacavir, AZT, aciclovir, aldesleukin, amprenavir, atazanavir, atovaquone, azithromycin, cidofovir, clarithromycin, clindamycin, cotrimoxazol, DDC, DDI, dapsone, daunorubicin, delavirdin, doxorubicin, efavirenz, emtricitabin, enfurvitide, erythropoetin, ethambutol, filgrastim, fluconazole, fosamprenavir, foscarnet, G-CSF, ganciclovir, indinavir, interleukin-2, interferon alpha, isoniazid, itraconazole, lamivudin, lenograstim, lopinavir, nelfinavir, nevirapine, pentamidine, pyrimethamine, ribavirin, rifabutin, rifampicin, ritonavir, saquinavir, stavudin, sulfadiazin, T-20, tenofovir, tipranavir, valganciclovir, voriconazol and 3TC,
22. Calcium antagonists
    Dihydropyridines (Nifedipine type)
    Nifedipine, nitrendipine, felodipine, amlodipine, lercanidipine, nimodipine, nicardipine, lacidipine, isradipine, nisoldipine, nilvadipine and manidipine
    Phenylalkylamines (Verapamil type)
    Verapamil, gallopamil and fendilin
    Benzothiazepine (Diltiazem type)
    Diltiazem.

Pharmaceutical active substances of especial interest are amphotericin B, cyclosporin A, aciclovir, ritonavir, paclitaxel, taxane, ketoconazole, itraconazole, ibuprofen, naproxen, omeprazole, pantoprazole, loratadine, desloratadine, loperamide and daglutril.

According to one embodiment mode, the frozen matrix thus obtained is dispersed in the frozen state in a cooled non-solvent as the external phase by means of conventional stirring methods or dispersion methods, so that a mixture of ice and external phase is formed.

If necessary, surfactants, antiflocculants (e.g. sodium citrate) and polymeric stabilisers can be added to the external phase.

Medium or high shear and/or cavitation forces are then applied to the dispersion thus produced directly and before the melting of the frozen dispersed matrix. Medium shear forces can be applied by rotor-stator stirring systems (power density: $10^6/10^7$ W/m$^3$) or alternative devices such as for example toothed discs. Alternatively devices with higher power density in the range from $10^9/10^{13}$ W/m$^3$ can be used, by means of which high forces can then be applied to the suspensions Examples of such devices are jet homogenisers or piston-gap homogenisers (e.g. devices of the Avestin, APV Gaulin or Niro Soavi series) or ultrasound generators from the firm Sonics.

Example 1 shows the implementation of the mode of the invention described above with the use of the drug substance amphotericin B. After 5 homogenisation cycles, a suspension with an average particle size of 143 nm, which was determined by means of photon correlation spectroscopy was obtained. After seven days' storage, the average particle size increased only by 64 nm to 207 nm, although the solvent used dimethyl sulphoxide was not removed from the system. This example shows that with the use of the method according to the invention nanosuspensions with markedly improved storage stabilities in comparison with hydrosols can be attained.

According to another embodiment mode, the matrix obtained after freezing is carefully and slowly dried in a freeze-drying process (lyophilisation) before dispersion in the external phase, in order to remove the solvent used. This implementation mode is particularly suitable with the use of relatively toxic solvents, or when the solvent used is not miscible with the desired external phase. After the removal of the solvent, the matrix obtained is further processed analogously to the first embodiment mode.

Example 2 shows the implementation of this modification including freeze-drying. For the freezing of the amphotericin B solution, a freezing chest at a temperature of −20° C. was used, which resulted in rapid, but not sudden freezing of the solution. After 5 homogenisation cycles, the average particle size determined by PCS was 186 nm.

In contrast to this, in Example 3 the amphotericin B solution was shock frozen in liquid nitrogen. After 5 homogenisation cycles, the average particle size determined by PCS was 62 nm. It can thus be stated that the freezing rate has a marked influence on the particle size subsequently achievable. This can be explained in that faster freezing results in smaller crystals (Rudolf Voigt, Pharmaceutical Technology for Study and Profession, Ullstein Mosby, page 59-60), which can be better stabilised by the energy then applied.

In Example 4 the drug substance cyclosporin A was processed in accordance with the first embodiment mode, whereby after 15 homogenisation cycles an average particle size of 630 nm was determined by PCS.

In contrast to this, in Example 5 the second embodiment mode of the patent, i.e. with lyophilisation, was used. After 15 homogenisation cycles, particles with an average PCS diameter of 440 nm were obtained. Thus it is found that the use of the second embodiment mode generally results in a smaller particle size, however additional energy must also be applied for this in the form of the lyophilisation.

In order to be able to use the particles produced on the industrial scale, apart for adequate stability in the form of the suspension, the possibility of conversion into a dry, storable product is also necessary.

Example 6 shows the lyophilisation of the nanosuspension produced for Example 3. The lyophilisation resulted in a porous, dry product, from which a nanosuspension with approximately the same particle size as mentioned in Example 3 could be obtained again by reconstitution with distilled water.

Example 7 shows the lyophilisation of the nanosuspension produced for Example 5. Here also the lyophilisation with subsequent reconstitution resulted in a comparable particle size.

It can thus be stated that the method presented here is suitable for processing substances poorly soluble in water, and in particular also thermolabile and sensitive substances. With a few homogenisation cycles or by the application of a relatively low power density, nanosuspensions whose average particle size in some cases even lies far below 100 nm can be obtained. Moreover, the nanosuspensions created have very good stability and can easily be converted into dry products with the small particle size remaining the same.

The particle size determination was carried out using laser diffractometry (LD) and photon correlation spectroscopy (PCS). The laser diffractometry was carried out with a Coulter LS 230 (Beckman-Coulter, USA) and yields a volume-based particle size distribution as the result. The parameters enlisted for determination were the 50% (D 50%), 90% (D 90%) and 99% (D 99%) diameters. D 50% for example means that 50% of the particles based on their volume have a diameter below the stated value. The PCS analysis was carried out with a Zetasizer 4 (Malvern Instruments, GB). The PCS yields an average particle diameter (z-average) of the main population and a polydispersity index (PI) as a measure of the breadth of the particle size distribution. The PI for relatively narrow distributions lies between 0.1-0.2. Values greater than 0.5 and above point to a very broad particle size distribution.

A poorly soluble substance in the sense of this invention has a maximal solubility of 1%, preferably less than 0.1% and in particular less than 0.01% in the dispersion medium (stated in mass percent).

The invention is characterised in that particulate material in the nanometer range can be attained by application of a small number of homogenisation cycles or by a relatively brief exposure to shear and cavitation forces. After 1-5 cycles, the particle diameters are normally already below 1000 nm, very often below 400 nm and in the case of softer materials below 100 nm. An increase in the cycle number is only necessary in the case of hard to very hard substances, however at most 15 to 20 cycles are necessary.

The production of pharmaceutical active substances in the nanometer range is advantageous and conceivable for a great variety of application routes and use examples. In topical preparations for applications to the skin, nanocrystalline forms increase the saturation solubility, which results in improved penetration into the skin. For oral administration, the dissolution rate of poorly soluble active substances is markedly improved. The increased saturation solubility results in an increased concentration gradient, which in turn results in increased blood concentration levels. Parenteral administration via injections and infusions is also possible, during which the rapidly dissolving nanocrystals imitate the properties of a solution. A further application for drug substance nanocrystals would be ophthalmic agents, e.g. administration on or in the eye could result in an extended dwell time of the active substance on the eye.

The nanoparticles produced could also be introduced into other carrier systems and lead to advantages on account of their size. Drug substance nanocrystals can be positively charged through the use of suitable surfactants or stabilisers, which results in increased adhesivity on the skin and on products attached to the skin such as for example hair. Applications in the foodstuffs industry are also conceivable, poorly soluble additives could be better dispersed and divided into portions. In addition, nanocrystalline dyes for use in cosmetic products are conceivable, but also of colour pigments for various other applications. Nanocrystalline material can also find uses in the textile industry.

According to a further preferred embodiment, the present invention also describes a multistage process for the production of surface-modified active substance nanoparticles or nanosuspensions by high-pressure homogenisation of modified active substance material in the presence of various polymers or protective colloids with exclusion of the use of surfactants and/or emulsifiers. The modified active substance nanoparticles also have an average particle size from 10 nm to below 1000 nm. Present as a nanosuspension, the modified active substance nanoparticles are exclusively stabilised by the applied polyelectrolyte multilayer or polyelectrolyte multilayers and can either be used directly as a nanosuspension or be further processed to dry powders.

In general, for the stabilisation of the colloidal systems prepared in this manner, addition of surfactants, emulsifiers or polymeric stabilisers is necessary. For this, the surfactants are often used in the ratio 1:1 to 1:10 (surfactant to drug substance). Undesired effects can be caused by the surfactants used, such as for example allergic reactions.

However, the present preferred embodiment enables the production of nanosuspensions with exclusion of surfactants through the production of surface-modified (polymer-coated) active substance nanoparticles.

According to the state of the art, coating of for example micro and nanocrystals (template particles) is achieved by dispersing a dispersion of template particles (crystals for coating) or solid template particles in a salt-containing liquid phase which contains the components necessary for the coating (capsule formation) in dissolved form, and a capsule shell is formed by precipitation of the components (EP 01,305,109 B1).

Hitherto, in the coating of template particles, the starting point was always coating material in dissolved form (polyelectrolyte solutions). The polyelectrolyte chains present in dissolved form can however cause the onset of a strong, sometimes irreversible aggregation of the template particles via so-called bridge formation, in particular when the template particle dispersion has not been stabilised by means of surfactants, stabilisers or other surface-active substances.

The coating of the template particles with polyelectrolyte multilayers is effected stepwise, in other words the template particles are coated with several (at least two) alternating layers of oppositely charged polyelectrolytes. After each individual coating step, the template particle as a rule have to be separated from the excess polymer by filtration, centrifugation or dialysis (as described in U.S. Pat. No. 6,833,192 or WO 2004/047977 A1), before the next polyelectrolyte layer can be applied. This results in relatively large losses of freely mobile template particles owing to filter residues on the one hand and irreversible aggregation and agglomeration during the centrifugation on the other.

The present embodiment is thus a combined method for the production of active substance nanoparticles with simultaneous surface modification for the purpose of decreasing the tendency of the particles produced to aggregation and agglomeration.

Figure 1:
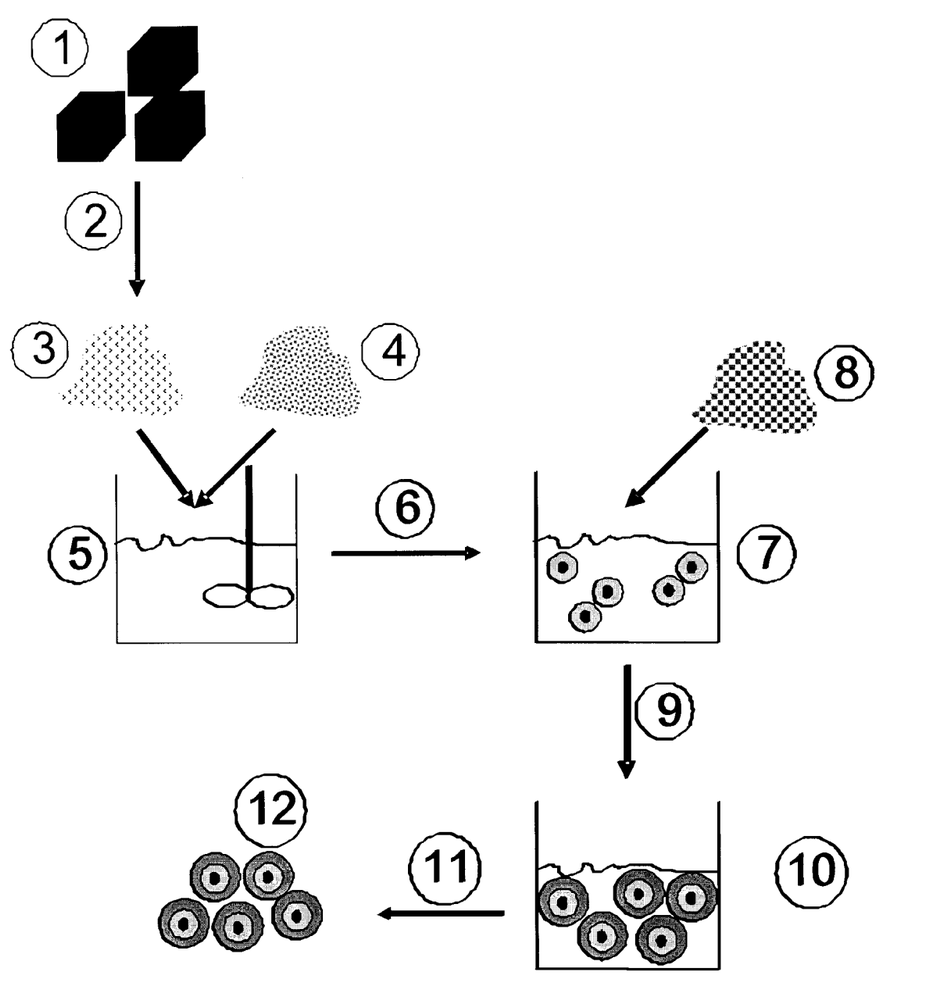

Also this embodiment is characterised in that the active substance nanoparticles to be coated are produced in the first process step by means of high-pressure homogenisation. For this, the poorly water-soluble or water-insoluble active substance (see FIG. 1, point 1) is dissolved in a suitable solvent and the resulting solution then frozen (see FIG. 1, point 2), so that a solid, frozen matrix is formed. Next, either the solvent is completely removed from the frozen matrix by lyophilisation or processing is continued with the frozen matrix. The modified active substance (see FIG. 1, point 3) is dispersed together with the powdered polymer 1 or protective colloid 1 (see FIG. 1, point 4) in an external phase by means of suitable mixers (e.g. UltraTurrax) (see FIG. 1, point 5). It is important that here only the polymer 1 or protective colloid 1 is soluble in the external phase. Next the dispersion of water-soluble or water-insoluble active substance and solid polymer 1 or protective colloid 1 is subjected to several high-pressure homogenisation cycles (see FIG. 1, point 6), so that a metastable nanosuspension is formed, wherein the surface of the active substance nanoparticles is occupied by polymer 1 or protective colloid 1 (see FIG. 1, point 7). Next, the polymer 2 or protective colloid 2 oppositely charged to polymer 1 or protective colloid 1 is added to this metastable nanosuspension (see FIG. 1, point 8). This mixture is then again homogenised (see FIG. 1, point 9), during which the pressure can be reduced compared to the initial homogenisation cycles ((FIG. 1, point 6), since the homogenisation no longer serves for particle pulverisation. The nanoparticles thus produced (see FIG. 1, point 10) have an oppositely directed surface charge compared to the particles of the metastable nanosuspension (FIG. 1, point 7). In addition, the nanosuspension formed is no longer metastable, but instead has excellent physical stability with no tendency to particle aggregation or agglomeration. These nano-suspensions thus produced can be used as a product or be further processed. By conventional drying processes (see FIG. 1, point 11), such as for example spray-drying, lyophilisation or simple filtration with subsequent drying of the filter cake, nanocrystalline active substance powders are produced (see FIG. 1, point 12) which can for example be filled into hard gelatine capsules or compressed into tablets.

The surface-modified particles produced by this embodiment of the invention also have an average particle size from 10 nm to <1000 nm, preferably from 100 nm to <1000 nm, most preferably from 200 nm to 500 nm.

Here also, the active substances to be processed can originate from a great variety of fields, i.e. pharmaceutical active substances, cosmetic active substances, but also additives for the foodstuffs industry and materials for other industrial fields can be processed, which should preferably be in the form of nanocrystalline material, such as for example dyes and dye pigments for paints and lacquers or for cosmetic applications.

A particular feature of this embodiment according to the invention is that the active substance nanoparticles whose surface properties are to be modified by means of polymer adsorption are produced directly in the process by high-pressure homogenisation with simultaneously occurring polymer coating. Furthermore, the process of particle size reduction is particularly effective owing to the use of specially modified starting material, which means that for the attainment of active substance particle sizes in the nanometer range (corresponding to point 6, FIG. 1) often only up to at most 5 homogenisation cycles have to be performed, in special cases only 3 homogenisation cycles, and especially only 1 homogenisation cycle.

In the processes for particle coating with polyelectrolyte multilayers according to the state of the art, the adsorption of polyelectrolytes takes place on the basis of opposite charge of the polyelectrolytes used, whereby for the attainment of so-called charge overcompensation (more polyelectrolytes are bound to the particle surface than is necessary for charge equalisation) an excess of polyelectrolytes and a certain salt content are necessary. In contrast to this, the method of the invention requires no addition of salt, since the particle coating takes place rather actively on account of the high pressures used, in other words the polyelectrolytes are deposited on the active substance particle surface under pressure. It is well known that the addition of salts to colloidal systems can decrease their physical stability owing to the reduction of the zeta potential. Because of the avoidance of salt addition, the attainable physical stability of the suspensions produced by the method according to the invention is markedly improved.

Both low molecular weight polyelectrolytes or polyions and also macromolecular polyelectrolytes, for example polyelectrolytes of biological origin, are suitable as the polyelectrolyte.

The active substance nanoparticles are coated with at least two polyelectrolyte layers, in other words with at least one positive and one negative polyelectrolyte layer (protective colloid layer). Polyelectrolytes are generally understood to mean polymers with ionically dissociable groups, which can be a component or a substituent of the polymer chain. Now the number of dissociable groups in polyelectrolytes is so great that the polymers in the dissociated form (also called polyions) are soluble in the liquid phase of the nanosuspension. Depending on the nature of the dissociable groups, polyelectrolyte are subdivided into polyacids and polybases.

On dissociation, polyacids lose protons with the formation of polyanions. Examples of polyacids are polymethacrylates, cellulose acetate phthalate (CAP), hydroxypropylmethylcellulose phthalate (HPMCP), hydroxypropylmethylcellulose acetate succinate (HPMCAS), polyacrylic acid, alginic acid, carboxymethylcellulose, dextran sulphate, ligninsulphonic acid, polyvinylsulphonic acid, polyvinylphosphonic acid, chondroitinsulphonic acid and salts thereof.

Usable biopolymers are for example gelatine A and gelatine B, chitosan and salts thereof, protamine sulphate, hyaluronic acid, polylysine acid, polylactic acid, carragenans, pectins, gum Arabic and nucleic acids.

Polybases contain protonatable groups, which are capable of taking up protons, e.g. by reaction with acids with salt formation. Examples of polybases with dissociable groups in the chain or side-chain are polyethylenimine, polyvinylamine and polyvinylpyridine. After their protonation, polybases are present as polycations.

A particular advantage of the surface modification according to this embodiment consists in that between the individual coating steps no separation of excess polyelectrolytes by separation processes such as centrifugation, filtration or dialysis have to be performed. Firstly, the quantities of polymer necessary can be determined in preliminary experiments or appropriately calculated, so that exactly the necessary quantity can be added, without a large polymer excess being necessary. Secondly, excess polymers present do not disturb the production process. Only the formation of active substance-free complexes from the oppositely charged polymers or protective colloids, which however have no adverse effects on the product properties, can then occur. Since separation steps during the coating of the active substance nanoparticles can be dispensed with, the process according to the invention is particularly suitable for use as a continuous process on the industrial scale.

Owing to the high energy which is introduced into the system during the high-pressure homogenisation and the simultaneously occurring particle coating, any aggregates of active substance nanoparticles that may form are immediately destroyed. Through the creation of a stable, very high zeta potential due to the application of the second oppositely charged polymer (FIG. 1, point 8) the active substance nanosuspension is very well stabilised and then has very good physical stability. The zeta potential (here only the absolute value, and not the sign, of the charge is decisive) of the nanosuspension produced by the process according to the invention, measured in water with a conductivity in the region of 50 μS at pH values between 4 to 7, lies in the range from 5 mV to 100 mV, preferably in the range from 20 mV to 80 mV, particularly preferably in the range from 30 mV to 60 mV.

Owing to the high surface charge and the stable adhesion of the polyelectrolyte layer to the active substance nanocrystals, both the nanosuspensions themselves and also the powders obtained by drying have excellent physical stability under the action of electrolyte.

A further advantage of the process according to the invention is the possibility of complete exclusion of surfactants during the production process. In contrast to the previous state of the art, it could be shown that colloidal active substance suspensions can be produced by high-pressure homogenisation even with complete exclusion of surfactants (see Examples 8 to 12). This is especially advantageous when the nanosuspensions prepared by the process according to the invention are to be used as medicaments, or further processed into medicaments. The exclusion of surfactants is of particular importance for the production of active substance nanosuspensions for parenteral administration.

EXAMPLE 1

400 mg of amphotericin B were dissolved in 10 mL of dimethyl sulphoxide. Liquid nitrogen was added to this solution, which resulted in immediate freezing of the drug substance solution. After the liquid nitrogen had evaporated, the porous matrix consisting of frozen dimethyl sulphoxide and amphotericin B thus obtained was dispersed in 30 g of an aqueous 1.1% sodium cholate solution (w/w) using an UltraTurrax (Janke & Kunkel, Germany) for 5 seconds at 9500 revolutions per minute and immediately homogenised in a MicronLab 40 high-pressure homogeniser (APV Gaulin, Germany) at 1500 bar with a device temperature of 10° C. After 5 homogenisation cycles, the average particle diameter, measured by photon correlation spectroscopy (PCS) was 143 nm with a polydispersity index (PI) of 0.252. The volume distributions determined by laser diffractometry (LD) were D50% 70 nm, D90% 209 nm and D99% 279 nm. After a storage time of 7 days at room temperature (RT) the average particle diameter measured by PCS was 207.1 nm and the volume distributions D50% 136.0 nm, D 90% 193.0 nm and D99% 452.0 nm.

EXAMPLE 2

400 mg of amphotericin B were dissolved in 10 mL of dimethyl sulphoxide. This solution was then frozen at −20° C. and then lyophilised in a Christ alpha I-5 lyophilisation apparatus (Christ-Apparatebau, Osterode, Germany). The porous matrix thus obtained was dispersed in 39.6 g of an aqueous 1.1% sodium cholate solution (w/w) using an UltraTurrax (Janke & Kunkel, Germany) for 10 seconds at 9500 revolutions per minute and immediately homogenised in a MicronLab 40 high-pressure homogeniser (APV Gaulin, Germany) at 1500 bar with a device temperature of 0° C. After 5 homogenisation cycles, the average particle diameter, measured by PCS was 186 nm with a PI of 0.411. The volume distributions were D50% 78 nm, D90% 238 nm and D99% 446 nm.

EXAMPLE 3

400 mg of amphotericin B were dissolved in 10 mL of dimethyl sulphoxide. Liquid nitrogen was then added to this solution, which resulted in immediate freezing of the drug substance solution. The frozen solution was then lyophilised in a Christ alpha I-5 lyophilisation apparatus (Christ-Apparatebau, Osterode, Germany). The porous matrix thus obtained was dispersed in 39.6 g of an aqueous 1.1% sodium cholate solution (w/w) using an UltraTurrax (Janke & Kunkel, Germany) for 10 seconds at 9500 revolutions per minute and immediately homogenised in a MicronLab 40 high-pressure homogeniser (APV Gaulin, Germany) at 1500 bar with a device temperature of 0° C. After 5 homogenisation cycles, the average particle diameter measured by PCS was 62 nm with a PI of 0.555. The volume distributions were D50% 60 nm, D90% 79 nm and D99% 98 nm.

EXAMPLE 4

400 mg of cyclosporin A were dissolved in 10 mL of ethanol. Liquid nitrogen was added to this solution, which resulted in immediate freezing of the drug substance solution. After the liquid nitrogen had evaporated, the porous matrix consisting of frozen ethanol and cyclosporin thus obtained was coarsely dispersed in 30 g of an aqueous 1.1% poloxamer 188 solution (w/w) using a spatula and immediately homogenised in a MicronLab 40 high-pressure homogeniser (APV Gaulin, Germany) at 1500 bar with a device temperature of 0° C. After 15 homogenisation cycles, the average particle diameter measured by PCS was 630 nm with a PI of 0.302. The volume distributions were D50% 794 nm, D90% 1717 nm and D99% 3857 nm.

EXAMPLE 5

400 mg of cyclosporin A were dissolved in a mixture of 10 mL of ethanol and 10 mL of dimethyl sulphoxide. Liquid nitrogen was added to this solution, which resulted in immediate freezing of the drug substance solution. The frozen solution was then lyophilised in a Christ alpha I-5 lyophilisation apparatus (Christ-Apparatebau, Osterode, Germany). The porous matrix thus obtained was dispersed in 39.6 g of an aqueous 1.1% poloxamer 188 solution (w/w) using an UltraTurrax (Janke & Kunke, Germany) for 10 seconds at 9500 revolutions per minute and immediately homogenised in a MicronLab 40 high-pressure homogeniser (APV Gaulin, Germany) at 1500 bar with a device temperature of 0° C. After 15 homogenisation cycles, the average particle diameter, measured by PCS was 440 nm with a PI of 0.264. The volume distributions were D50% 405 nm, D90% 1790 nm and D99% 2321 nm.

EXAMPLE 6

1 mL of the suspension obtained in Example 3 was treated with 10 mg of fructose. This mixture was at once frozen in liquid nitrogen. The frozen mixture was then lyophilised in a Christ alpha I-5 lyophilisation apparatus (Christ-Apparatebau, Osterode, Germany). The porous matrix thus obtained was resuspended in distilled water. The average particle diameter, measured by PCS, was 61 nm with a PI of 0.455.

EXAMPLE 7

1 mL of the suspension obtained in Example 3 was treated with 10 mg of fructose. This mixture was at once frozen in liquid nitrogen. The frozen mixture was then lyophilised in a Christ alpha I-5 lyophilisation apparatus (Christ-Apparatebau, Osterode, Germany). The porous matrix thus obtained was resuspended in distilled water. The average particle diameter, measured by PCS, was 574 nm with a PI of 0.444.

EXAMPLE 8

4.0 g of micronised ibuprofen were dispersed in 36.0 mL of acidified water (pH 2.5) with addition of 36.0 mg of solid powdered Eudragit E (cationic protective colloid 1) using an UltraTurrax (Jahnke & Kunkel, Germany) for 5 seconds at 9500 revolutions per minute. The resulting dispersion was homogenised in a Micron Lab 40 high-pressure homogeniser (APV Systems, Germany) at 1500 bar at room temperature. After 5 homogenisation cycles, the zeta potential of the resulting metastable crude suspension was determined. The value for the zeta potential (measured in water with a pH value adjusted to 3.8 and conductivity adjusted to 50 $\mu$S) was: 75.2 mV. After addition of 400 mg of solid, powdered polyacrylic acid (anionic protective colloid 2) (pH measurement/adjustment to pH 3.8) the metastable crude suspension was again homogenised for 5 cycles in a Micron Lab 40 high-pressure homogeniser (APV Systems, Germany) at 1500 bar at room temperature. As the end product, a physically stable, homogeneous suspension was obtained, which displayed neither a tendency to particle aggregation nor to agglomeration, which could be confirmed using an optical microscope. Next the zeta potential of the suspension was again determined (measured in water with a pH value adjusted to 3.8 and conductivity adjusted to 50 $\mu$S) and its value was: −22.7 mV.

EXAMPLE 9

4.0 g of ibuprofen were dissolved in 10.0 mL of ethanol. Liquid nitrogen was added to this solution, which resulted in immediate freezing of the drug substance solution. After the liquid nitrogen had evaporated, the porous matrix thus obtained consisting of frozen ethanol and ibuprofen was dispersed in 36.0 mL of acidified water (pH 2.5) with addition of 36.0 mg of solid powdered Eudragit E (cationic protective colloid 1) using an UltraTurrax (Jahnke & Kunkel, Germany) for 5 seconds at 9500 revolutions per minute and immediately homogenised in a Micron Lab 40 high-pressure homogeniser (APV Systems, Germany) at 1500 bar at room temperature. After 5 homogenisation cycles, the zeta potential of the resulting metastable crude suspension was determined. The value for the zeta potential (measured in water with a pH value adjusted to 3.8 and conductivity adjusted to 50 $\mu$S) was: 41.6 mV. After addition of 400 mg of solid, powdered polyacrylic acid (Carbopol 980) (anionic protective colloid 2) (pH measurement/adjustment to pH 3.8) the metastable crude suspension was again homogenised for 5 cycles in a Micron Lab 40 high-pressure homogeniser (APV Systems, Germany) at 1500 bar at room temperature. As the end product, a physically stable, homogeneous suspension was obtained, which displayed neither a tendency to particle aggregation nor to agglomeration, which could again be confirmed using an optical microscope. Next the zeta potential of the suspension was again determined (measured in water with a pH value adjusted to 3.8 and conductivity adjusted to 50 $\mu$S) and its value was: −31.3 mV.

EXAMPLE 10

4.0 g of ibuprofen were dissolved in 10.0 mL of acetone. Liquid nitrogen was added to this solution, which resulted in immediate freezing of the drug substance solution. After the liquid nitrogen had evaporated, the porous matrix thus obtained consisting of frozen acetone and ibuprofen was dispersed in 36.0 mL of acidified water (pH 2.5) with addition of 36.0 mg of solid powdered Eudragit E (cationic protective colloid 1) using an UltraTurrax (Jahnke & Kunkel, Germany) for 5 seconds at 9500 revolutions per minute and immediately homogenised in a Micron Lab 40 high-pressure homogeniser (APV Systems, Germany) at 1500 bar at room temperature. After 5 homogenisation cycles, the zeta potential of the resulting metastable crude suspension was determined. The value for the zeta potential (measured in water with a pH value adjusted to 3.8 and conductivity adjusted to 50 $\mu$S) was: 6.2 mV. After addition of 400 mg of solid, powdered polyacrylic acid (Carbopol 980) (anionic protective colloid 2) (pH measurement/adjustment to pH 3.8) the metastable crude suspension was again homogenised for 5 cycles in a Micron Lab 40 high-pressure homogeniser (APV Systems, Germany) at 1500 bar at room temperature. As the end product, a physically stable, homogeneous suspension was obtained, which displayed neither a tendency to particle aggregation nor to agglomeration, which could again be confirmed using an optical microscope. Next the zeta potential of the suspension was again determined (measured in water with a pH value adjusted to 3.8 and conductivity adjusted to 50 $\mu$S) and its value was: −31.9 mV.

EXAMPLE 11

0.4 g of hydrocortisone acetate were dissolved in 10 mL of dimethyl sulphoxide. Liquid nitrogen was then added to this solution, which resulted in immediate freezing of the drug substance solution. The frozen solution was then lyophilised for 48 hrs in a Christ alpha I-5 lyophilisation apparatus (Christ-Apparatebau, Osterode, Germany). The porous matrix thus obtained was treated with 200 mg of solid, powdered chitosan hydrochloride (cationic protective colloid 1) and dispersed in 39.2 g of water using an UltraTurrax (Jahnke & Kunkel, Germany) for 5 seconds at 9500 revolutions per minute and immediately homogenised in a Micron Lab 40 high-pressure homogeniser (APV Systems, Germany) at 1500 bar at room temperature. The metastable crude suspension obtained after 5 homogenisation cycles was observed under the microscope and micrographs were taken. The value of the zeta potential (measured in water with a pH value adjusted to 6.5 and a conductivity adjusted to 50 µS) was: 47.8 mV. After addition of 400 mg of solid, powdered gelatine B (anionic protective colloid 2) (pH measurement/adjustment to pH 7.0) the metastable crude suspension was again homogenised for 5 cycles in a Micron Lab 40 high-pressure homogeniser (APV Systems, Germany) at 1500 bar at room temperature. As the end product, a physically stable, homogeneous suspension was obtained, which displayed neither a tendency to particle aggregation nor to agglomeration, which could be confirmed using an optical microscope. Next the zeta potential of the suspension was again determined (measured in water with a pH value adjusted to 6.5 and a conductivity adjusted to 50 µS), and its value was: −16.9 mV.

EXAMPLE 12

0.4 g of hydrocortisone acetate were dissolved in 10 mL of dimethyl sulphoxide. Liquid nitrogen was then added to this solution, which resulted in immediate freezing of the drug substance solution. The frozen solution was then lyophilised for 48 hrs in a Christ alpha I-5 lyophilisation apparatus (Christ-Apparatebau, Osterode, Germany). The porous matrix thus obtained was treated with 200 mg of solid, powdered chitosan hydrochloride (cationic protective colloid 1) and dispersed in 39.2 g of water using an UltraTurrax (Janke & Kunkel, Germany) for 5 seconds at 9500 revolutions per minute and immediately homogenised in a Micron Lab 40 high-pressure homogeniser (APV Systems, Germany) at 1500 bar at room temperature. The metastable crude suspension obtained after 5 homogenisation cycles was observed under the microscope and micrographs were taken. The value of the zeta potential (measured in water with a pH value adjusted to 6.5 and a conductivity adjusted to 50 µS) was: 47.8 mV. After addition of 400 mg of solid, powdered polyacrylic acid (Carbopol 980) (anionic protective colloid 2) (pH measure-ment/adjustment to pH 7.0) the metastable crude suspension was again homogenised for 5 cycles in a Micron Lab 40 high-pressure homogeniser (APV Systems, Germany) at 1500 bar at room temperature. As the end product, a physically stable, homogeneous suspension was obtained, which displayed neither a tendency to particle aggregation nor to agglomeration. Next the zeta potential of the suspension was again determined (measured in water with a pH value adjusted to 6.5 and a conductivity adjusted to 50 µS), and its value was: −34.2 mV.

The average particle diameter, measured by photon correlation spectroscopy (PCS), was 1025.4 nm with a polydispersity index (PI) of 0.294. The volume distributions determined by laser diffractometry (D) were D50% 414 nm, D90% 1977 nm and D95% 2926 nm.

The invention claimed is:

1. Method for the gentle production of ultrafine particle suspensions comprising:
dissolving a substance in solid form that is insoluble in water or poorly soluble in water in a suitable solvent to form a solution comprising the substance dissolved in the solvent;
freezing the solution to form a solid matrix of the frozen solution;
dispersing the solid matrix of the frozen solution in the frozen state in a dispersion medium comprising water to form a first dispersion of frozen solution particles dispersed in the dispersion medium; and
applying high forces in the range of $10^9$ to $10^{13}$ W/m$^3$ using high pressure homogenization to the first dispersion prior to the melting of the frozen solution particles to disintegrate and melt the frozen solution particles, and when the frozen solution is melted the dispersion medium causes precipitation of a solid substance in a mixture of the solvent and the dispersion medium to form a second particle suspension comprising solid substance particles suspended in the mixture of the solvent and dispersion medium and the application of high forces during the precipitation inhibits growth of a size of the solid substance particles, to form the solid substance particles having an average particle size, determined by photon correlation spectroscopy (PCS), of below 1000 nm.

2. Method according to claim 1, wherein the substance to be dissolved in the suitable solvent is a drug active substance, a cosmetic active substance, an additive for foodstuffs, a dye or a pigment.

3. Method according to claim 1, wherein the solvent used for the dissolution of the substance insoluble in water or poorly soluble in water comprises at least one solvent selected from hydrophilic liquids, mixtures of water with liquids completely or partially miscible with water or hydrophilic liquids, or liquids immiscible with water.

4. Method according to claim 1, wherein the solution also contains at least one component selected from additives and dispersion-stabilising substances, wherein the concentrations per component, based on the weight, are in the range from 1-90%.

5. Method according to claim 4, wherein the stabilising substances include compounds from among poloxamers, poloxamines, ethoxylated mono- and diglycerides, ethoxylated lipids and lipoids, ethoxylated fatty alcohols and alkylphenols, ethoxylated fatty acid esters, polyglycerine ethers and ester, lecithins, esters and ethers of sugars or sugar alcohols with fatty acids or fatty alcohols, phospholipids and sphingolipids, sterols, esters or ethers thereof and mixtures thereof of these compounds.

6. Method according to claim 4, wherein the stabilising substances include egg lecithin, soya lecithin or hydrogenated lecithin, mixtures thereof or mixtures of one or both lecithins with one or more phospholipid components, cholesterol, cholesterol palmitate, stigmasterol or other sterols.

7. Method according to claim 4, wherein the stabilisers include diacetyl phosphate, phosphatidyl-glycerol, saturated or unsaturated fatty acids, sodium cholate, peptising agents or amino acids.

8. Method according to claim 4, wherein the solution contains one or more viscosity-increasing substances.

9. Method according to claim 4, wherein the solution in addition contains one or more further additives.

10. Method according to claim 1, complete freezing of the precise part of the solution produced to be frozen is effected within less than 60 seconds.

11. Method according to claim 1, wherein the dispersion medium further comprises at least one medium selected from water-miscible liquids, non-aqueous media or organic solvents or lipophilic liquids, in which the substance is poorly soluble or insoluble.

12. Method according to claim 1, wherein the first dispersion contains at least one component selected from further additives and dispersion-stabilising substances, wherein the concentrations per component, based on the weight, are in the range from 1-90%.

13. Method according to claim 12, wherein the dispersion-stabilising substances include compounds from among the poloxamers, poloxamines, ethoxylated mono- and diglycerides, ethoxylated lipids and lipoids, ethoxylated fatty alcohols and alkylphenols, ethoxylated fatty acid esters, polyglycerine ethers and esters, lecithins, esters and ethers of sugars or sugar alcohols with fatty acids or fatty alcohols, phospholipids and sphingolipids, sterols, esters or ethers thereof and mixtures thereof of these compounds.

14. Method according to claim 12, wherein the dispersion-stabilising substances include egg lecithin, soya lecithin or hydrogenated lecithin, mixtures thereof or mixtures of one or both lecithins with one or more phospholipid components, cholesterol, cholesterol palmitate, stigmasterol or other sterols.

15. Method according to claim 12, wherein the stabilisers include dicetyl phosphate, phosphatidyl-glycerol, saturated or unsaturated fatty acids, sodium cholate, peptising agents or amino acids.

16. Method according to claim 1, wherein at least one viscosity-increasing substance is contained in the dispersion.

17. Method according to claim 1, wherein the dispersion also contains at least one additive selected from sugars or sugar alcohols, sodium citrate, sodium hydrogen phosphate, sodium dihydrogen phosphate, sodium chloride, potassium chloride, calcium chloride or glycerine.

18. Method according to claim 1, wherein a high-pressure homogeniser is utilized and the homogenisation pressure is above 100 bar.

19. Method according to claim 1, wherein the solid substance particles which are contained in the second particle suspension are separated or dried.

20. Method according to claim 1, wherein the second particle suspension obtained or the solid substance particles obtained after separation from the second particle suspension is/are further processed to intermediate or end products.

21. Method according to claim 1, wherein the second particle suspension is spray-dried or lyophilised.

22. Method according to claim 1, wherein the high forces are effected by high-pressure homogenisation and simultaneously a surface modification of the solid substance particles formed is carried out, and wherein the method further comprises:
    conducting the high-pressure homogenisation in the presence of a protective colloid 1 (polyelectrolyte 1) in solid form for at least one homogenization cycle to form a nanosuspension having a desired particle size;
    adding a second protective colloid 2 (polyelectrolyte 2) in solid form, oppositely charged to the protective colloid 1 (polyelectrolyte 1), to the nanosuspension to form a suspension;
    subjecting the suspension to high-pressure homogenization until a finely divided, homogeneous, stable nanosuspension is obtained; and
    isolating the solid substance particles contained in the homogenous, stable nanosuspension by separation.

23. Method according to claim 22, wherein the solid substance particles produced by high-pressure homogenisation, which for the purpose of surface modification and stabilisation, are coated with at least two polyelectrolyte layers, oppositely charged at a certain pH value of the dispersion medium, are drug substance nanocrystals.

24. Method according to claim 22, wherein the modification of the surface of the solid substance particles is achieved by means of at least one first coating comprising at least one first polyelectrolyte present as a polycation at a certain pH value of the dispersion medium and a second coating of a second polyelectrolyte present as a polyanion at a certain pH value of the dispersion medium.

25. Method according to claim 22, wherein the polyelectrolytes used include at least one polyelctrolyte selected from polymethacrylates, cellulose acetate phthalate (CAP), hydroxypropylmethyl-cellulose phthalate (HPMCP), hydroxypropylmethylcellulose acetate succinate (HPM-CAS), polyacrylic acid, alginic acid, carboxymethylcellulose, dextran sulphate, ligninsulphonic acid, polyvinylsulphonic acid, polyvinyl-phosphonic acid, chondroitinsulphonic acid, gelatine A, gelatine B, chitosan, Protmain sulphate, hyaluronic acid, polylysine acid, polylactic acid, carragenans, pectins, gum Arabic, nucleic acids, polyethylenimine, polyvinyl-amine and polyvinylpyridine, and respectively the various salts, free bases or free acids thereof.

26. Method according to claim 22, wherein the resulting surface-modified active substance particles have a zeta potential, measured in water with a conductivity in the range from 50 µS, at pH values between 4 to 7, in the range from 5 mV to 100 mV, where exclusively the absolute value of the zeta potential and not its sign is relevant.

27. Method according to claim 1, wherein the solvent used for the dissolution of the substance insoluble in water or poorly soluble in water comprises at least one solvent selected from alcohols, mixtures of water with liquids completely or partially miscible with water or alcohols, or liquids immiscible with water.

28. Method according to claim 1, wherein the solvent used for the dissolution of the solid insoluble in water or poorly soluble in water comprises at least one solvent selected from N-methyl-2-pyrrolidinone, 2-pyrrolidone, dimethyl-acetamide, ethanol, methanol, isopropanol, acetone, chloroform, dichloromethane, dimethyl sulphoxide, n-propanol, glycerol, ethylene glycol, dimethylformamide, dimethylacetamide or acids and bases.

29. Method according to claim 1, wherein the solution also contains at least one component selected from surfactants, stabilisers of the antiflocculant and polymer type, and inert fillers, wherein the concentrations per component, based on the weight, are in the range from 1-20%.

30. Method according to claim 1, wherein the solution also contains at least one component selected from surfactants, stabilisers of the antiflocculant and polymer type, and inert fillers, wherein the concentrations per component, based on the weight, are below 0.01-5%.

31. Method according to claim 4, wherein the solution contains at least one component selected from cellulose ethers and esters, polyvinyl derivatives, alginates, xanthans, pectins, polyacrylates, poloxamers and poloxamines, polyvinyl alcohol or polyvinylpyrrolidone.

32. Method according to claim 4, wherein the solution in addition contains at least one component selected from glucose, mannose, trehalose, mannitol and sorbitol, fructose, sodium citrate, sodium hydrogen phosphate, sodium dihydrogen phosphate, sodium chloride, potassium chloride, glycerine, dyes or pigment.

33. Method according to claim 1, wherein complete freezing of the solution to be frozen is effected within less than 30 seconds.

34. Method according to claim 1, wherein complete freezing of the solution to be frozen is effected within less than 10 seconds.

35. Method according to claim 1, wherein complete freezing of the solution to be frozen is effected within less than 1 second.

36. Method according to claim 1, wherein the first dispersion also contains one or more components selected from additives, surfactants, stabilisers of the antiflocculant and polymer type, or inert fillers, wherein the concentrations per component, based on the weight, lie in the range from 1-20%.

37. Method according to claim 1, wherein the first dispersion also contains one or more components selected from additives, surfactants, stabilisers of the antiflocculant and polymer type, or inert fillers, wherein the concentrations per component, based on the weight, are below 0.01-5%.

38. Method according to claim 1, wherein the first dispersion contains at least one component selected from the group of cellulose ethers and esters, polyvinyl derivatives, alginates, xanthans, pectins, polyacrylates, poloxamers and poloxamines, polyvinyl alcohol or polyvinyl-pyrrolidone.

39. Method according to claim 1, wherein the applied energy is applied by homogenisers of the piston-gap type, of the jet-stream type, or a French Press.

40. Method according to claim 18, wherein the homogenisation pressure is above 500 bar.

41. Method according to claim 18, wherein the homogenisation pressure is above 1500 bar.

42. Method according to claim 18, wherein the homogenisation pressure is at or above 2000 bar.

43. Method according to claim 18, wherein the high pressure homogeniser is used for attaining an average PCS particle size below 1000 nm, and the number of homogenisation cycles is less than 5.

44. Method for production of particle nanosuspensions comprising:

a) dissolving a substance in a solid form and having a water solubility of less than 1 mass % in a solvent to form a solution comprising the substance dissolved in the solvent;

b) freezing the solution from a) to form a solid matrix of frozen solution;

c) dispersing the solid matrix in the frozen state in a dispersion medium comprising water to form a first dispersion of frozen solution particles dispersed in the dispersion medium; and d) applying high forces at a power density of $10^9$ to $10^{13}$ $W/m^3$ using high pressure homogenization to the first dispersion prior to the melting of the frozen solution particles to disintegrate and melt the frozen solution particles and when the frozen solution is melted the dispersion medium causes precipitation of a solid substance in a mixture of the solvent and the dispersion medium to form a second particle suspension comprising solid substance particles suspended in the mixture of the solvent and dispersion medium and the application of high forces during the precipitation inhibits growth of a size of the solid substance particles, to form the solid substance particles having an average particle size, determined by photon correlation spectroscopy (PCS), of below 1000 nm.

* * * * *